(12) United States Patent
Sjong et al.

(10) Patent No.: US 8,911,961 B2
(45) Date of Patent: Dec. 16, 2014

(54) METHODS FOR DETECTING LIVE PATHOGENS

(75) Inventors: Angele Sjong, Louisville, CO (US); Kraig Anderson, Burlingame, CA (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/823,305

(22) PCT Filed: May 1, 2012

(86) PCT No.: PCT/US2012/035993
§ 371 (c)(1),
(2), (4) Date: Mar. 14, 2013

(87) PCT Pub. No.: WO2013/165398
PCT Pub. Date: Nov. 7, 2013

(65) Prior Publication Data
US 2014/0011223 A1    Jan. 9, 2014

(51) Int. Cl.
*C12Q 1/04* (2006.01)
*C12Q 1/10* (2006.01)
*G01N 21/41* (2006.01)
*C12Q 1/48* (2006.01)
*G01N 21/45* (2006.01)

(52) U.S. Cl.
CPC *G01N 21/41* (2013.01); *C12Q 1/48* (2013.01); *G01N 21/45* (2013.01); *G01N 2333/195* (2013.01); *G01N 2333/9108* (2013.01)
USPC .......................................... 435/34; 435/288.7

(58) Field of Classification Search
None
See application file for complete search history.

(56) References Cited

U.S. PATENT DOCUMENTS

| 6,773,706 B2 * | 8/2004 | Mazmanian et al. ...... 424/185.1 |
| 2003/0022178 A1 | 1/2003 | Schneewind et al. |

FOREIGN PATENT DOCUMENTS

| CN | 101603075 | 12/2009 | |
| JP | 2009189325 | * 12/2009 | .............. C12P 21/02 |
| WO | WO-2007/082075 | 7/2007 | |

OTHER PUBLICATIONS

Pacholski et al. "Small molecule detection by reflective interferometric Fourier transform spectroscopy" Phys. Status. Solidi A (2009) 206:6 1318-1321.*

Orosco et al. "Real-time monitoring of enzyme activity in a mesoporous silicon double layer" Nat Nanotechnol (2009) 4:4 255-258.*
Marraffini et al "Sortase C-mediated anchoring of Basl to the cell wall envelope of *Bacillus anthracis*" Journal of Bacteriology (2007) 189:17 6435-6436.*
Jonsson et al. "The role of *Staphylococcus aureus* sortase A and sortase B in murine arthritis" Microbes and Infection (2003) 5:775-780.*
Hinton et al. "Antimicrobial activity of potassium hydroxide and lauric acid against microorganisms associated with poultry processing" Journal of Food Protection 2006 69:7 1611-1615.*
www.brenda-enzymes.org (EC 3.4.22.7 sortase B 2010).*
Blinka et al., "Enhanced microcontact printing of proteins on nanoporous silica surface" Nanotechnology, Oct. 15, 2010, 21(41); 23 pages.
Boekhorst et al., "Genome-Wide Detection and Analysis of Cell Wall-Bound Proteins with LPxTG-Like Sorting Motif," J. Bacteriology, 2005, 187(14), pp. 4928-4934.
Chan, Selena et al. "Identification of Gram Negative Bacteria Using Nanoscale Silicon Microcavities," J. Am. Chem. Soc. 2001, 123, pp. 11797-11798.
International Search Report and Written Opinion for PCT/US2012/035993, mailed May 31, 2012.
Jonkheijm et al., "Chemical Strategies for Generating Protein Biochips," Agnew. Chem. Int. Ed. 2008, 47, pp. 9618-9647.
Losic, D., et al., "Self-ordering electrochemistry: a simple approach for engineering nanopore and naotube arrayes for emerging applications," Australian Journal of Chemistry, 2001, 64(3), pp. 294-301.
Lu, Jinghui, et al., "Detection of Label-Free Biomolecules by Wavelength-Scanning Reflective Interferometric Sensing," American Institute of Chemical Engineers Annual Meeting, Nov. 2004, Advances in Biosensor I, 7 pages.
Lu, Jinghui et al., "Reflective Interferometric Detection of Label-Free Oligonucleotides," Anal. Chem., 2004, 76, pp. 4416-4420.
Massad-Ivanir, Naama et al., "Engineering Nanostructured Porous $SiO^2$ Surfaces for Bacterial Detection via Direct Cell Capture", Anal. Chem., 2011, pp. 3282-3289.
Nelson et al., "A Biosynthetic Strategy for Re-engineering the *Staphylococcus aureus* Cell Wall with Non-native Small Molecules" ACS Chemical Biology, 2010, 5(12), pp. 1147-1155.
Pacholski, Claudia et al., "Reflective Interferometric Fourier Transform Spectroscopy: A Self-Compensating Label-Free Immunosensor Using Double-Layers of Porous SiO2," J. Am. Chem. Soc., 2006, 128, pp. 4250-4252.
Pacholski, Claudia et al., "Biosensing Using Porous Silicon Double-Layer Interferometers: Reflective Interferometric Fourier Transform Spectroscopy," J. Am Chem. Soc., 2005, vol. 127, pp. 11636-11645.

* cited by examiner

*Primary Examiner* — Suzanne M Noakes
*Assistant Examiner* — Gerard Lacourciere
(74) *Attorney, Agent, or Firm* — Foley & Lardner LLP

(57) ABSTRACT

Disclosed are methods and kits pertaining to detecting live bacterial pathogens using sortase enzymes and reflective spectroscopy such as reflective interferometry.

26 Claims, 1 Drawing Sheet

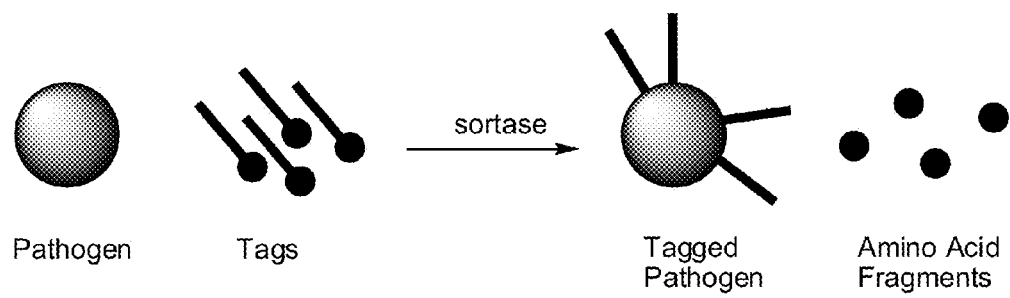
Pathogen    Tags    Tagged Pathogen    Amino Acid Fragments
FIGURE 2
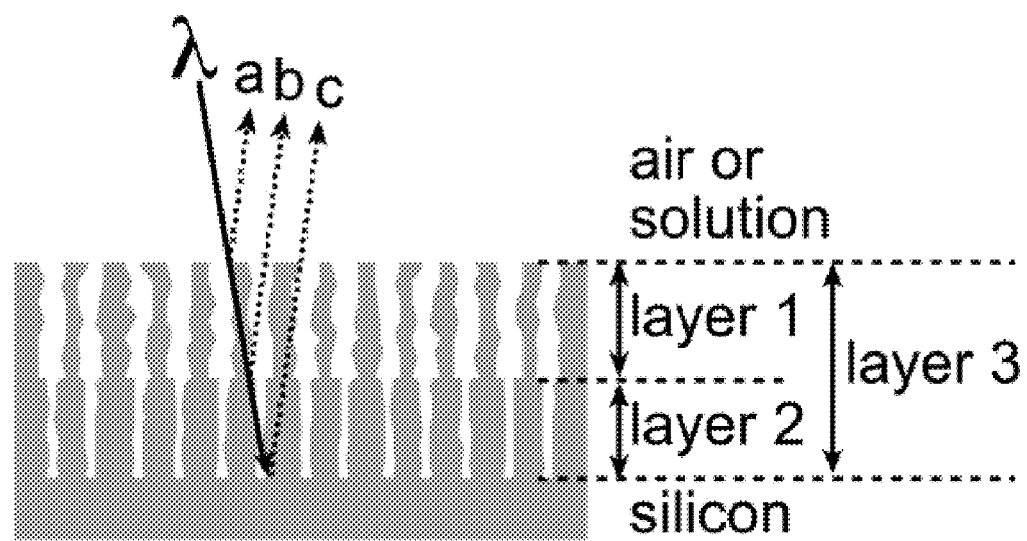

METHODS FOR DETECTING LIVE PATHOGENS

CROSS REFERENCE TO RELATED APPLICATIONS

This application is the U.S. National Stage of PCT/US2012/035993, filed on May 1, 2012, the entire contents of which is incorporated herein by reference.

SEQUENCE LISTING

The instant application contains a Sequence Listing which has been submitted in ASCII format via EFS-Web and is hereby incorporated by reference in its entirety. Said ASCII copy, created on May 21, 2014, is named 091619-0791_SL.txt and is 7,900 bytes in size.

TECHNICAL FIELD

This disclosure relates generally to methods pertaining detection of live pathogens. In certain embodiments, the disclosure relates to detecting enzymatic by-products of live pathogens using reflective interferometry.

BACKGROUND

The following description is provided to assist the understanding of the reader. None of the information provided or references cited is admitted to be prior art.

Sensitive and accurate detection of bacterial contamination in food products and liquids is important for ensuring the protection of human and animal safety. Presently, many methods of detecting bacterial contamination in food and liquid utilize monoclonal antibody binding to detect specific bacterial pathogens. However, the sensitivity of assays using antibodies is limited since a typical bacterial cell includes few binding sites for a typical selective antibody. Moreover, existing antibody detection schemes react to their binding target regardless of whether the target is part of a live cell. Thus, these techniques are prone to false positives and increased background from dead cells and/or cell detritus. Consequently, even with sophisticated detectors, live food pathogen detection limits are still typically high, approximately $10^4$ to $10^5$ colony forming units per milliliter.

SUMMARY

The methods described herein relate to detecting live bacterial pathogens in a sample and involve cleavage of peptides by enzymes in the pathogen, and detecting products of the cleaved enzymes using light reflectance.

In one aspect, the present technology provides methods for detecting one or more live bacterial pathogens in a sample. The methods may include: contacting the sample with one or more bacterial sortase substrates and a biosensor having a porous membrane, wherein the porous membrane excludes intact sortase substrates and admits the product of a cleaved sortase substrate; measuring the reflectivity spectrum of the biosensor; and comparing the reflectivity spectrum to that of a biosensor not contacted with the sample, wherein an altered reflectivity spectrum indicates the presence of one or more live bacterial pathogens in the sample.

In another aspect, the present technology provides methods for detecting one or more live foodborne bacterial pathogens in a food matrix. The methods may include: contacting the food matrix with a biosensor having a porous membrane and one or more bacterial sortase substrates, wherein the porous membrane excludes intact sortase substrates and admits the product of a cleaved sortase substrate; measuring the reflectivity spectrum of the biosensor using Reflective Interferometric Fourier Transform Spectroscopy (RIFTS); and comparing the reflectivity spectrum to that of a biosensor not contacted with the food matrix, wherein an altered reflectivity spectrum indicates the presence of one or more live bacterial pathogens in the food matrix.

In yet another aspect, the present technology provides a kit for detecting one or more live bacterial pathogens in a sample. The kit includes one or more bacterial sortase substrates; and a biosensor comprising a porous membrane, wherein the porous membrane excludes intact sortase substrates and admits the product of a cleaved sortase substrate.

In some embodiments of the methods described herein, measuring the reflectivity spectrum of the biosensor is accomplished using one or more of Reflective Interferometric Fourier Transform Spectroscopy (RIFTS), grazing angle x-ray reflectivity, gonioreflectometry, or spectral reflectivity.

In some embodiments of the methods and kits described herein, the biosensor comprises a self-compensating interferometric biosensor. In some embodiments the porous membrane of the biosensor is made of at least silicon dioxide or aluminum oxide. In some embodiments, the porous membrane has at least a base layer and a surface layer, each layer comprising interconnected pores, wherein the base layer has pores of a smaller diameter than the surface layer and excludes the product of a cleaved sortase substrate, and wherein the base layer contacts a solid support.

In some embodiments of the methods and kits described herein, the one or more sortase substrates are attached to the porous membrane. In some embodiments, the one or more sortase substrates are selected from one more peptides comprising the amino acid sequence Leu-Pro-X-Thr-Gly (SEQ ID NO. 1), wherein X may be any proteinogenic amino acid. In some embodiments, the one or more sortase substrates are selected from one more peptides comprising the amino acid sequence Asn-X-Thr-Asn (SEQ ID NO: 2), wherein X may be any proteinogenic amino acid. In some embodiments, the one or more sortase substrates are selected from one more peptides comprising the amino acid sequence Leu-Pro-Asn-Thr-Ala (SEQ ID NO: 3). In some embodiments, the one or more sortase substrates are one or more peptides of the amino acid sequence Leu-Pro-X-Thr-Gly (SEQ ID NO. 1), wherein X may be any proteinogenic amino acid. In some embodiments, the one or more sortase substrates are one or more peptides comprising the amino acid sequence Asn-X-Thr-Asn (SEQ ID NO: 2), wherein X may be any proteinogenic amino acid. In some embodiments, the one or more sortase substrates are one or more peptides comprising the amino acid sequence Leu-Pro-Asn-Thr-Ala (SEQ ID NO: 3). In some embodiments, the proteinogenic amino acid is selected from the group consisting of alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, and tyrosine.

In some embodiments of the methods and kits described herein, the presence of one or more live bacterial pathogens in the sample results in proteolytic cleavage of the one or more peptides, thereby releasing the product of a cleaved sortase substrate. In some embodiments, the sortase substrate is a sortase A substrate. In some embodiments, the product of a cleaved sortase substrate is Gly, Asn, or Ala.

In some embodiments of the methods and kits described herein, the product of a cleaved sortase A substrate enters the surface layer of the porous membrane, thereby causing an alteration in the reflectivity spectrum of the surface layer.

In some embodiments of the methods and kits described herein, the one or more bacterial pathogens have at least genera selected from the group consisting of *Listeria, Clostridium, Enterococcus, Staphylococcus, Streptococcus, Actinobacter, Bacillus,* and *Corynebacterium*.

In some embodiments of the methods described herein, the food matrix comprises fluids associated with dairy, meat, fish, fruit, and vegetables.

In some embodiments of the kits described herein, the kit has at least one or more positive controls, that have one or more bacterial sortase enzymes specific for the one or more bacterial sortase substrates. In some embodiments, the one or more positive controls have live bacteria. In some embodiments, the one or more positive controls have recombinant enzymes. In some embodiments of the kits described herein, the kit has at least one or more negative controls. In some embodiments the one or more negative controls include a solution that does not contain protein. In some embodiments, the one or more negative controls include a protein or enzyme that does not cleave sortase substrates. In some embodiments, the one or more negative controls include a bacterial protease that does not cleave sortase substrates. In some embodiments, the one or more negative controls include non-pathogenic live bacteria that do not express sortase enzymes.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 is a schematic showing the steps of sortase cleavage of a peptide.

FIG. 2 is a schematic representation of a cross-section of a two-layer biosensor and light beams being applied and reflected.

DETAILED DESCRIPTION

Unless otherwise stated, the singular forms "a," "an," and "the" as used herein include plural reference.

As used herein, the term "sortase" or "sortase enzyme" refers to a prokaryotic enzyme having a catalytic domain with activity capable of selectively cleaving a backbone peptide bond of a polypeptide at a sortase recognition sequence and catalyzing a transpeptidation reaction which results in the formation of an amide bond between the terminal carboxyl group created by the cleavage and a surface protein of the cell wall of a cell. Sortase is present in almost all Gram-positive bacteria, as well as a few Gram-negative bacteria and Archaea.

The term "polypeptide" or "peptide" as used herein refers to two or more amino acids linked by a peptide (i.e., amide) bond between the carboxyl terminus of one amino acid and the amino terminus of another. The term "polypeptide" or "peptide" includes a protein. Where the polypeptide includes a sortase recognition sequence, the polypeptide may be cleave by a sortase enzyme in the manner described above. The term "peptide" may be combined with a prefix indicating the number of amino acids in the peptide, e.g., a "pentapeptide" is a peptide of five amino acids.

Sortase Enzymes and Specificity

Sortases are a family of bacterial enzymes (transpeptidases) that covalently anchor proteins made by the bacteria to the cell wall envelope of gram-positive, some gram-negative bacteria. Many gram-positive bacteria are pathogenic to humans. Table 1 below lists exemplary gram-positive bacteria and the diseases they cause in humans.

TABLE 1

Gram-Positive Bacterial Pathogens and Corresponding Diseases

| Pathogen | Disease |
| --- | --- |
| *Listeria* | meningitis |
| *Clostridium* | botulism, tetanus, gas gangrene, and pseudomembranous colitis |
| *Enterococcus* | Urinary tract infections, bacteremia, bacterial endocarditis, meningitis |
| *Staphylococcus* | Sialadenitis (food poisoning) |
| *Streptococcus* | Strep throat, meningitis, bacterial pneumonia |
| *Bacillus* | anthrax and gastroenteritis |
| *Corynebacterium* | Diphtheria |

The transpeptidation reaction catalyzed by sortases is a cleavage of a surface protein substrate at a peptide motif near the cell wall sorting signal, leaving an acyl protein intermediate and a short peptide that includes the cell wall sorting signal. The acyl protein intermediate then undergoes a transpeptidation reaction with a peptidoglycan precursor, and binds to the peptidoglycan in the cell wall.

Sortases are characterized in four different classes (A, B, C, D). Each of the sortase classes cleaves a different peptide motif, and some class members cleave multiple peptide motifs. Class A sortases are used to anchor cell wall proteins involved with cell adhesion, immune evasion, internalization, and can act as phage receptors. Class B sortases anchor proteins to the cell wall that are used to acquire iron. Class C sortases assemble pili on the bacterial surface, and class D sortases anchor proteins to the cell wall during sporulation of bacilli and *streptomyces*.

Class A Sortase typically cleaves the consensus peptide motif LPXTG (Leu-Pro-X-Thr-Gly; SEQ ID NO. 1), where X represents any proteinogenic amino acid. (As will be understood by those of skill in the art, the one and three letter codes for L-alpha amino acids used throughout this disclosure are well known in the art and have their art-accepted meanings.) Class A Sortase cleaves between the threonine and the glycine. The cleaved cell sorting peptide maintains the glycine residue at its amino terminus, and the cleaved protein binds to the peptidoglycan at the threonine residue. Class B Sortase cleaves a consensus motif of NXTN (Asn-X-Thr-Asn; SEQ ID NO: 2) between threonine and asparagine where X represents any proteinogenic amino acid. Class C Sortase cleaves the consensus motif LPXTG (SEQ ID NO: 1) where X represents any proteinogenic amino acid and accepts the lysine within the sequence YPKN (Tyr-Pro-Lys-Asn; SEQ ID NO: 4) as a residue for covalently linking the threonine on the cell wall peptide. Class D Sortase cleaves the consensus motif LPNTA (SEQ ID NO: 3) between the threonine and the alanine.

Organism-specific cleavage motifs also exist for substrates cleaved by sortase A. For example, *Lactobacillus johnsonii* has a conserved substrate cleavage motif of LPQTG (Leu-Pro-Gln-Thr-Gly; SEQ ID NO: 5), and its sortase A cleaves between the threonine and glycine, while *Listeria monocytogenes* has a conserved substrate cleavage motif of LPXTGD (Leu-Pro-X-Thr-Gly-Asp; SEQ ID NO: 7), in which peptide cleavage by sortase A occurs between the threonine and the glycine, resulting in a two-residue peptide of GD. Variation in cleavage motifs among bacterial genera is described in Boekhurst et al., J Bacteriol. 2005 July; 187(14):4928-34.

Table 2 lists exemplary cleavage motifs for sortase A that are specific to certain gram-positive bacteria.

TABLE 2

Examples of Class A Sortase cleavage motifs

| Bacteria | Sortase Class | Cleavage Motif |
|---|---|---|
| Lactobacillus johnsonii | A | LPQTG (SEQ ID NO: 5) |
| Lactobacillus plantarum | A | LPQTXE (SEQ ID NO: 6) |
| Listeria monocytogenes | A | LPXTGD (SEQ ID NO: 7) |
| Streptomyces coelicolor | A | LAXTG (SEQ ID NO: 8) |

Boekhurst et al used in silico analysis of 199 bacterial genomes to predict sortase cleavage sequences. In particular, species-specific pentapeptides were predicted for: *Bacillus anthracis* A2012, *Bacillus anthracis* Ames, *Bacillus anthracis* Ames 0581, *Bacillus anthracis* str *Sterne, Bacillus cereus* ATCC14579, *Bacillus cereus* ATCC 10987, *Bacillus cereus* ZK, *Bacillus halodurans, Bacillus licheniformis* ATCC 14580, *Bacillus licheniformis* DSM 13, *Bacillus subtilis, Bacillus thuringiensis konkukian, Bifidobacterium longum, Bradyrhizobium japonicum, Clostridium acetobutylicum, Clostridium perfringens, Clostridium tetani* E88, *Corynebacterium diphtherias, Enterococcus faecalis* V583, *Lactobacillus johnsonii* NCC 533, *Lactobacillus plantarum, Lactococcus lactis, Listeria innocua, Listeria monocytogenes, Listeria monocytogenes* 4b F2365, *Methanopyrus kandleri, Oceanobacillus iheyensis, Shewanella oneidensis, Staphylococcus aureus* MW2, *Staphylococcus aureus* Mu50, *Staphylococcus aureus* N315, *Staphylococcus aureus aureus* MRSA252, *Staphylococcus aureus aureus* MSSA476, *Staphylococcus epidermidis* ATCC 12228, *Streptococcus agalactiae* 2603, *Streptococcus agalactiae* NEM316, *Streptococcus mutans, Streptococcus pneumoniae* R6, *Streptococcus pneumoniae* TIGR4, *Streptococcus pyogenes, Streptococcus pyogenes* MGAS10394, *Streptococcus pyogenes* MGAS315, *Streptococcus pyogenes* MGAS8232, *Streptococcus pyogenes* SSI-1, *Streptomyces avermitilis, Streptomyces coelicolor, Tropheryma whipplei* TW08 27, and *Tropheryma whipplei* Twist. The amino acid sequences associated with the species-specific pentapeptides disclosed by =Boekhorst et al., for the above microorganisms are summarized in Table 3, below.

TABLE 3

Amino acid residues known or predicted to be present in pentapeptide sortase recognition sequences.
(N-terminus) $Xaa_1$-$Xaa_2$-$Xaa_3$-$Xaa_4$-$Xaa_5$ (C-terminus)

| $Xaa_1$ | $Xaa_2$ | $Xaa_3$ | $Xaa_4$ | $Xaa_5$ |
|---|---|---|---|---|
| L, N, A, I, G, V, P, F, or Y | P, S, E, G, K, A, D, V, or L | K, A, N, Q, E, T, P, S, H, D, I, R, V, M, F, L, Y, or G | T, A, K, G, S, Y, E, M, V, or L | G, A, S, D, N, V, Q, E, K, or P |

The sortase substrates of the present technology may include, but are not limited to, any of the sortase recognition sequences embraced by Table 3. Thus, in some embodiments, the sortase substrate of the present technology includes the peptide sequence of Formula I.

$$Xaa_1\text{-}Xaa_2\text{-}Xaa_3\text{-}Xaa_4\text{-}Xaa_5 \qquad I$$

wherein each of $Xaa_1$, $Xaa_2$, $Xaa_3$, $Xaa_4$, and $Xaa_5$ is selected from the indicated amino acids in Table 3. For example, the polypeptide may be a pentapeptide with any of the following sequences: LPKTG (SEQ ID NO: 9), LPNTG (SEQ ID NO:10), LPETG (SEQ ID NO:11), LPQTG (SEQ ID NO:12), LPATG (SEQ ID NO:13), LPNTA (SEQ ID NO:14), LAETG (SEQ ID NO:15), or NPQTN (SEQ ID NO:16). It will be understood by those of skill in the art that the peptide sequences represented by Formula I are read from left to right, with the N-terminus on the left of each residue and the C-terminus on the right, and that each pair of adjacent residues are linked via a peptide bond between the C-terminus of one residue and the N-terminus of the adjacent residue.

In some embodiments of the present technology, the sortase substrate of the present technology is selected from the group consisting of the formulae in Table 4, wherein each of $Xaa_1$, $Xaa_2$, $Xaa_3$, $Xaa_4$, and $Xaa_5$ are selected from the indicated amino acids in Table 3.

TABLE 4

| Formula | Sequence | SEQ ID NO: |
|---|---|---|
| IVA | Leu-Pro-$Xaa_3$-Thr-$Xaa_5$ | 17 |
| IVB | Leu-Pro-$Xaa_3$-Thr-Gly | 18 |
| IVC | Leu-Pro-$Xaa_3$-$Xaa_4$-Gly | 19 |
| IVD | Leu-Pro-$Xaa_3$-Ala-Gly | 20 |
| IVE | Leu-Pro-$Xaa_3$-Thr-Ser | 21 |
| IVF | Leu-Pro-$Xaa_3$-Thr-Asn | 22 |
| IVG | Leu-Ala-$Xaa_3$-Thr-Gly | 23 |
| IVH | Leu-Ser-$Xaa_3$-Thr-Gly | 24 |
| IVI | Ile-Pro-$Xaa_3$-Thr-Gly | 25 |
| IVJ | Phe-Pro-$Xaa_3$-Thr-Gly | 26 |
| IVK | Leu-Pro-$Xaa_3$-Thr-Ala | 27 |

In some embodiments of the present technology, the sortase substrate includes Formula IVD and $Xaa_3$ is selected from any of A, E, H, K, L, N, Q, S, or T. In other embodiments, the sortase substrate has Formula IVE and $Xaa_3$ is selected from any of D, K, N, Q, S, or T. In other embodiments, the sortase substrate has Formula IVF and $Xaa_3$ is selected from any of K, M, N, Q, or T. In others, the sortase substrate has Formula IVG and $Xaa_3$ is selected from any of A, D, E, F, H, K, L, N, R, S, or Y. In other embodiments, the sortase substrate has Formula IVH and $Xaa_3$ is selected from any of F, N, or S. In other embodiments, the sortase substrate has Formula IVI and $Xaa_3$ is selected from any of D, E, K, M, N, Q, or R. In other embodiments, the sortase substrate has Formula IVJ and $Xaa_3$ is selected from any of K, Q, or S. In other sortase substrate, the polypeptide has Formula IVK and $Xaa_3$ is selected from any of D, E, K, or N.

In certain embodiments, the sortase substrate of Formula I includes a sequence selected from AKKEK (SEQ ID NO: 28), FPKTG (SEQ ID NO: 29), FPQTG (SEQ ID NO: 30), FPSTG (SEQ ID NO: 31), GPDTA (SEQ ID NO: 32), IPALG (SEQ ID NO: 33), IPDTG (SEQ ID NO: 34), IPETG (SEQ ID NO:

35), IPKTG (SEQ ID NO: 36), IPMTG (SEQ ID NO: 37), IPNTG (SEQ ID NO: 38), IPQTG (SEQ ID NO: 39), IPRTG (SEQ ID NO: 40), IVKTG (SEQ ID NO: 41), LAATG (SEQ ID NO: 42), LADTG (SEQ ID NO: 43), LAETG (SEQ ID NO: 44), LAHTG (SEQ ID NO: 45), LAFTG (SEQ ID NO: 46), LAKTG (SEQ ID NO: 47), LALTG (SEQ ID NO: 48), LANTG (SEQ ID NO: 49), LARTG (SEQ ID NO: 50), LASTG (SEQ ID NO: 51), LAYTG (SEQ ID NO: 52), LAETP (SEQ ID NO: 53), LEKTN (SEQ ID NO: 54), LGATG (SEQ ID NO: 55), LGNTG (SEQ ID NO: 56), LLKTG (SEQ ID NO: 57), LPAAG (SEQ ID NO: 58), LPEAG (SEQ ID NO: 59), LPHAG (SEQ ID NO: 60), LPKAG (SEQ ID NO: 61), LPLAG (SEQ ID NO: 62), LPNAG (SEQ ID NO: 63), LPQAG (SEQ ID NO: 64), LPSAG (SEQ ID NO: 65), LPTAG (SEQ ID NO: 66), LPKAN (SEQ ID NO: 67), LPEKG (SEQ ID NO: 68), LPALG (SEQ ID NO: 69), LPQMN (SEQ ID NO: 70), LPDTA (SEQ ID NO: 71), LPETA (SEQ ID NO: 72), LPKTA (SEQ ID NO: 73), LPNTA (SEQ ID NO: 74), LPFSG (SEQ ID NO: 75), LPSSG (SEQ ID NO: 76), LPQTD (SEQ ID NO: 77), LPATG (SEQ ID NO: 78), LPDTG (SEQ ID NO: 79), LPETG (SEQ ID NO: 80), LPFTG (SEQ ID NO: 81), LPGTG (SEQ ID NO: 82), LPHTG (SEQ ID NO: 83), LPITG (SEQ ID NO:129), LPKTG (SEQ ID NO: 84), LPLTG (SEQ ID NO: 85), LPMTG (SEQ ID NO: 86), LPNTG (SEQ ID NO: 87), LPQTG (SEQ ID NO: 88), LPRTG (SEQ ID NO: 89), LPSTG (SEQ ID NO: 90), LPTTG (SEQ ID NO: 91), LPVTG (SEQ ID NO: 92), LPYTG (SEQ ID NO: 93), LPKTN (SEQ ID NO: 94), LPMTN (SEQ ID NO: 95), LPNTN (SEQ ID NO: 130), LPQTN (SEQ ID NO: 96), LPTTN (SEQ ID NO: 97), LPDTS (SEQ ID NO: 98), LPKTS (SEQ ID NO: 99), LPNTS (SEQ ID NO: 100), LPQTS (SEQ ID NO: 0101), LPSTS (SEQ ID NO: 102), LPETV (SEQ ID NO: 103), LPIVG (SEQ ID NO: 104), LPIYS (SEQ ID NO: 105), LSNTG (SEQ ID NO: 106), LSSTG (SEQ ID NO: 107), LSFTG (SEQ ID NO: 108), NAKTN (SEQ ID NO: 109), NAKTS (SEQ ID NO: 110), NKKSA (SEQ ID NO: 111), NPKTG (SEQ ID NO: 112), NPQTG (SEQ ID NO: 113), NPQTN (SEQ ID NO: 114), NPTKQ (SEQ ID NO: 115), NDTAV (SEQ ID NO: 131), NPKSS (SEQ ID NO: 116), NSKTA (SEQ ID NO: 117), PETGE (SEQ ID NO: 118), PKTGE (SEQ ID NO: 119), VPTGV (SEQ ID NO: 120), VANTG (SEQ ID NO: 121), VPDTG (SEQ ID NO: 122), VPPTG (SEQ ID NO: 123), YPKTG (SEQ ID NO: 124), or YPRTG (SEQ ID NO: 125).

Engineered Peptides as Sortase Substrates

Because of the variety of sortases and species-specific cleavage motifs, peptides containing a sortase cleavage motif can be used as a cleavable marker attached to the biosensor contemplated herein. FIG. 1 is a schematic of a bacterium contacting peptides containing a cleavage motif and cleaving the peptide to release one portion of the peptide and covalently binding the other portion.

Peptides containing a sequence susceptible to sortase cleavage may be modified or synthesized in a variety of configurations. In one peptide configuration, the sortase cleavage sequence is at the carboxy terminus of the peptide. In that case, cleavage by a sortase results in a peptide shortened by one or two amino acids. For example, a peptide having a carboxy terminus with the sequence LPXTG (SEQ ID NO: 1), will give two cleavage products: a peptide terminating in LPXT and a free glycine (G). Similarly, a peptide with a carboxy terminus of LPKTGD (SEQ ID NO: 126) can be cleaved by sortase A from *Listeria monocytogenes*, leaving a two-residue peptide of glycine and aspartic acid (GD).

In another peptide configuration, the sortase cleavage sequence is at least two amino acid residues away from the carboxy terminus (two residues towards the N-terminus), so that sortase cleavage results in two peptides. For example, the sortase cleavage sequence has 5 amino acid residues, such as 5 lysines, that follow the cleavage sequence and make up the peptide's carboxy terminus. In another example, the sortase cleavage sequence is in the middle of a longer peptide.

Peptides can also be modified with small molecules other than amino acids. Peptides having sortase recognition sequences have been engineered to contain heterologous molecular labels such as fluorescein and biotin (Nelson et al, ACS Chem Biol. 2010 Dec. 17; 5(12):1147-55). These engineered peptides were used to incorporate the molecular labels into the cell wall of *Staphylococcus aureus* up to 6500 polypeptides per cell.

The sortase substrates of the present technology are readily synthesized using standard peptide coupling techniques and reagents well known in the art, such as those described in *Peptide Synthesis Protocols*, Pennington, M. W., Dunn, B. M. (Eds.) Humana Press, Inc., New Jersey, 1994 and in Bodansky, M. and A. Bodansky, A. *The Practice of Peptide Synthesis*, Springer-Verlag, New York 1984. The polypeptides may be synthesized in solution phase, or may be synthesized using solid phase resins and/or supports (e.g., rink resins, amide resins, polystyrene resins, and the like). The synthesis may be automated.

Fabrication of Two-Layer Biosensor

The biosensor contemplated herein may be fabricated in two layers, stacked one on top of the other. Each layer is porous, and has different diameter pores. The top layer of the biosensor that will be exposed to sample has larger diameter pores than the bottom layer. The pores in each layer are connected, such that a single pore is formed, with a wider section above and a narrower section below. FIG. 2 shows a schematic representation of a cross-section of a two-layer biosensor and its pores. The diameter of the larger diameter pore in layer 1 is configured such that an amino acid tag or small peptide tag cleaved by sortase A can easily enter the length of the pore. The diameter of the smaller pore in layer 2 is configured to exclude an amino acid tag or small peptide tag from the length of the pore.

The biosensor can be fabricated from mesoporous silicon or from anodic aluminum oxide. Methods of etching and electrochemistry techniques can be used to form the porous layers of the biosensor, for example as described in Pacholski et al 2005, Pacholski et al 2006, and Losic et al (Pacholski et al, J. Am. Chem. Soc. 2005, 127, 11636-11645; Pacholski et al, J. Am. Chem. Soc. 2006, 128, 4250-4252; Losic et al, Australian Journal of Chemistry, 64(3) 294-301, 2011). Example 1 describes an etching technique for forming the two-layer biosensor.

Attachment of Peptides to Surface of Biosensor

Peptides used to detect the presence of a live bacteria can be attached to a two-layer biosensor either covalently or non-covalently, both of which are known in the art. See Jonkheijm et al, Angew. Chem. Int. Ed. 2008, 47, 9618-9647 for descriptions of potential methods of peptide attachment.

Peptide adsorption to silicon can be used as a method of attachment. Nanoporous silicon has been shown to be capable of adsorbing peptides without covalent modification by Pacholski et al, 2005 and Pacholski et al 2006 (J. Am. Chem. Soc. 2005, 127, 11636-11645 and J. Am. Chem. Soc. 2006, 128, 4250-4252).

Covalent attachment of peptides can be accomplished by adding the peptides to functionalized silicon, for example, silicon having N-hydroxysuccinimide (NHS)-activated carboxylic acids. Following exposure of the peptide to the functionalized silicon, the amino terminus of the peptides reacts with the functional group and become covalently bound. Functionalization of silicon can be accomplished, for example, by removing the oxide layer of the silicon with hydrofluoric acid (HF) and then reacting the hydrogen terminated surface with functionalized alkenes. In another method, the silicon can be oxidized with ionized gas and functionalized using organo silanes. Microcontact printing and microstamping are also potential methods of precisely applying and covalently attaching peptides to silicon (see Jonkheijm et al, Angew. Chem. Int. Ed. 2008, 47, 9618-9647; Blinka et al Nanotechnology. 2010 Oct. 15; 21(41):415302).

Detection of Light Reflectance from Two-Layer Biosensor

Light reflectance from a two-layer biosensor can be measured in a variety of ways. Reflective Interferometric Fourier Transform Spectroscopy (RIFTS) is a method of detecting the reflectivity spectrum of the two-layer biosensor and resolving the individual components by fast Fourier transform (FFT). Light beams applied to the two-layer biosensor create three different interfering light beams that correspond to three FFT peaks. FIG. 2 shows a schematic of a two-layer biosensor, with the applied light beam (labeled as lambda), and the reflected beams labeled a, b, and c. Following detecting of the interfering light beams and fast Fourier transformation, FFT peaks corresponding to layer 1, layer 2, and layer 3 (the sum of layers 1 and 2 of the biosensor) are seen (see FIG. 2). The FFT peak for layer 2 can be calculated by subtracting the FFT peak intensity for layer 1 from layer 3.

A shift in the FFT peaks that correlate with a given layer indicates changes in amino acid or peptide concentration of the solution in the pores of that layer. Thus, changes in layer 1 following exposure of the biosensor to a sample, indicate entry of peptides and/or peptide fragments into the solution. Layer 2 of the biosensor is the portion of the biosensor that allows the biosensor to be self-compensating. Because peptides and/or amino acids are excluded from layer 2, the FFT spectrum for that layer will only change relative to reflectivity changes brought about by exposure to a sample liquid (as well as instrument variability) and allow the data to be corrected accordingly. Detection of amino acid and/or peptide fragments is accomplished by either calculating the ratio of intensities of the FFT spectrum peaks for layer 1 and layer 2, or by calculating the weighted difference in the frequencies of the FFT spectrum peaks from layer 1 and layer 2. Specific methods and algorithms disclosing RIFTS and FFT may be found, for example, in Pacholski et al, J. Am. Chem. Soc. 2005, 127, 11636-11645 and Pacholski et al, J. Am. Chem. Soc. 2006, 128, 4250-4252.

Other methods of measuring and detecting changes in spectral reflectance include: grazing angle x-ray reflectivity, also known as grazing-incidence small-angle X-ray scattering (GISAXS); gonioreflectometry, and spectral reflectivity.

Controls

The methods and kits described herein may contain one or more positive controls, one or more negative controls, or both positive and negative controls. Examples of positive controls may include lyophilized or soluble sortase enzymes that can cleave a sortase substrate (e.g. sortase A, sortase B, etc.), as well as non-pathogenic live bacteria that have extracellular expression of a sortase enzyme (e.g. *lactobacillus acidophilus*, or soil bacteria). Examples of negative controls include solutions that do not contain any proteins, lyophilized or solubilized enzymes or other proteins that do not cleave sortase substrates, as well as non-pathogenic live bacteria that do not express sortase enzymes. For example, a negative control can be lyophilized or solubilized bacterial proteases that do not cleave sortase substrates (e.g. thermolysin). Alternatively, a microorganism lacking sortase may be used (e.g., isogenic *S. aureus*).

EXAMPLES

The present compositions, methods and kits, thus generally described, will be understood more readily by reference to the following examples, which are provided by way of illustration and are not intended to be limiting of the present methods and kits. The following is a description of the materials and experimental procedures used in the Examples.

Example 1

Creation of a Silicon Two-Layer Porous Biosensor

A silicon (Si) two-layer porous biosensor is fabricated using electrochemical etching, with a short period of high applied current (11 seconds at 500 mA/cm$^2$; producing layer 1 pores of about 50 to 100 nm) followed by a longer period at low current (55 seconds at 167 mA/cm$^2$; producing layer 2 pores of less than 20 nm). The current is applied to a doped ($10^{-3}$Ω-cm) p-type (100)-oriented single crystal Si wafer in ethanolic HF solution. To prevent corrosion in aqueous solution, siloxy-terminated porous Si surfaces were prepared by thermal oxidation. The oxidation increases the hydrophilicity of porous Si, allowing water to effectively infiltrate the pores.

Example 2

Detecting Bacteria Using a Pentapeptide Adsorbed to a Biosensor

A biosensor having the nanostructure described in Example 1 has a surface coating of peptides having the sequence LPKTGD (SEQ ID NO: 126), a sequence recognized and cleaved by sortase A in *Listeria monocytogenes*. The peptides are adsorbed to the surface of the biosensor. The biosensor is exposed to a light source, and the reflected light beams from layer 1 and layer 2 are measured.

Fluid from a food item is then applied to the biosensor and allowed to incubate. During the incubation, living *Listeria monocytogenes* present in the fluid cleave the LPKTGD (SEQ ID NO: 126) peptides on the surface of the biosensor, producing a small, soluble GD peptide (glycine-aspartic acid). The soluble GD peptide enters the pores of layer 1.

The surface of the biosensor is then re-exposed to a light source and the reflected light beams from layer 1 and layer 2 are measured again. The reflectance data before and after adding the fluid sample are analyzed using fast Fourier transformation, and then compared to determine the presence or absence of GD peptide fragments. The presence of GD peptides in layer 1 indicates the presence of *Listeria monocytogenes* in the fluid.

Example 3

Detecting Bacteria Using a Shortened Internalin A Protein Adsorbed to a Biosensor A biosensor having the nanostructure described in Example 1 has a surface coating of a shortened Internalin A protein (SEQ ID NO:132). The protein has the sequence of residues 1-771 of GenBank Acc. No. NP_463962.1 and terminates at the carboxy terminus with the amino acid sequence LPTTG (SEQ ID NO: 91), a sequence recognized and cleaved by sortase A in *Listeria monocytogenes*. The protein is adsorbed to the surface of the biosensor. The biosensor is exposed to a light source, and the reflected light beams from layer 1 and layer 2 are measured. The sequence of GenBank Acc. No. NP_463962.1 is set forth in SEQ ID NO:134.

Fluid from a food item is then applied to the biosensor and allowed to incubate. During the incubation, living *Listeria monocytogenes* present in the fluid cleave the shortened Internalin A protein on the surface of the biosensor, producing soluble glycine residues that enter the pores of layer 1.

The surface of the biosensor is then re-exposed to a light source and the reflected light beams from layer 1 and layer 2 are measured again. The reflectance data before and after adding the fluid sample are analyzed using fast Fourier transformation, and then compared to determine the presence or absence of glycine residues. The presence of glycine in layer 1 indicates the presence of *Listeria monocytogenes* in the fluid.

Example 4

Detecting Bacteria Using a Modified Internalin A Protein Adsorbed to a Biosensor A biosensor having the nanostructure described in Example 1 has a surface coating of a modified Internalin A protein (SEQ ID NO:0133). The protein has the sequence of residues 1-771 of GenBank Acc. No. NP_463962.1, with the addition of five lysine residues at the C-terminus. The protein terminates at the carboxy terminus with the amino acid sequence LPTTGKKKKK (Leu-Pro-Thr-Thr-Gly-Lys-Lys-Lys-Lys-Lys; SEQ ID NO: 127). The protein is adsorbed to the surface of the biosensor. The biosensor is then exposed to a light source, and the reflected light beams from layer 1 and layer 2 are measured.

Fluid from a food item is then applied to the biosensor and allowed to incubate. During the incubation, living *Listeria monocytogenes* present in the fluid cleave the modified Internalin A on the surface of the biosensor, producing a small, soluble peptide of sequence GKKKKK (Gly-Lys-Lys-Lys-Lys-Lys; SEQ ID NO: 128). The soluble GKKKKK peptide (SEQ ID NO: 128) enters the pores of layer 1.

The surface of the biosensor is then re-exposed to a light source and the reflected light beams from layer 1 and layer 2 are measured again. The reflectance data before and after adding the fluid sample are analyzed using fast Fourier transformation, and then compared to determine the presence or absence of GKKKKK peptides (SEQ ID NO: 128). The presence of GKKKKK peptides (SEQ ID NO: 128) in layer 1 indicates the presence of *Listeria monocytogenes* in the fluid.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for detecting *Listeria monocytogenes* in a food matrix, the method comprising:
   contacting the food matrix with one or more bacterial sortase substrates, wherein the one or more sortase substrates consist of one or more peptides selected from the group consisting of the amino acid sequence set forth in SEQ ID NO:126, SEQ ID NO:132, or SEQ ID NO:133, and a biosensor comprising a porous membrane, wherein the porous membrane excludes intact sortase substrates and admits the product of a cleaved sortase substrate;
   measuring the reflectivity spectrum of the biosensor; and
   comparing the reflectivity spectrum to that of a biosensor not contacted with the food matrix,
   wherein an altered reflectivity spectrum indicates the presence of *Listeria monocytogenes* in the food matrix.

2. The method of claim 1, wherein measuring the reflectivity spectrum of the biosensor is accomplished using one or more of Reflective Interferometric Fourier Transform Spectroscopy (RIFTS), grazing angle x-ray reflectivity, gonioreflectometry, or spectral reflectivity.

3. The method of claim 1, wherein the biosensor comprises a self-compensating interferometric biosensor.

4. The method of claim 1 wherein the porous membrane comprises silicon dioxide or aluminum oxide.

5. The method of claim 1, wherein the porous membrane comprises at least a base layer and a surface layer, each layer comprising interconnected pores, wherein the base layer comprises pores of a smaller diameter than the surface layer and excludes the product of a cleaved sortase substrate, and wherein the base layer contacts a solid support.

6. The method of claim 1, wherein the one or more sortase substrates are attached to the porous membrane.

7. The method of claim 1, wherein the one or more sortase substrates further comprise one or more peptides comprising the amino acid sequence Leu-Pro-X-Thr-Gly (SEQ ID NO. 1), wherein X may be any proteinogenic amino acid.

8. The method of claim 1, wherein the one or more sortase substrates further comprise one or more peptides comprising the amino acid sequence Leu-Pro-Asn-Thr-Ala (SEQ ID NO: 3).

9. The method of claim 7, wherein the proteinogenic amino acid is selected from the group consisting of alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, and tyrosine.

10. The method of claim 1, wherein the presence of *Listeria monocytogenes* in the food matrix results in proteolytic cleavage of the one or more peptides, thereby releasing the product of a cleaved sortase substrate.

11. The method of claim 10, wherein the product of a cleaved sortase substrate is Gly-Asp or Gly-Lys-Lys-Lys-Lys-Lys (SEQ ID NO: 128).

12. The method of claim 10, wherein the product of a cleaved sortase substrate enters the surface layer of the porous membrane, thereby causing an alteration in the reflectivity spectrum of the surface layer.

13. The method of claim 1, wherein the food matrix comprises fluids associated with dairy, meat, fish, fruit, or vegetables.

14. A kit for detecting *Listeria monocytogenes* in a food matrix, the kit comprising:
   one or more bacterial sortase substrates, wherein the one or more sortase substrates consist of one or more peptides selected from the group consisting of the amino acid sequence set forth in SEQ ID NO:126, SEQ ID NO:132, or SEQ ID NO:133; and
   a biosensor comprising a porous membrane, wherein the porous membrane excludes intact sortase substrates and admits the product of a cleaved sortase substrate.

15. The kit of claim 14, further comprising one or more positive controls comprising one or more bacterial sortase enzymes specific for the one or more bacterial sortase substrates.

16. The kit of claim 14, wherein the biosensor comprises a self-compensating interferometric biosensor.

17. The kit of claim 14, wherein the porous membrane comprises silicon dioxide or aluminum oxide.

18. The kit of claim 14, wherein the porous membrane comprises at least a base layer and a surface layer, each layer comprising interconnected pores, wherein the base layer comprises pores of a smaller diameter than the surface layer and excludes the product of a cleaved sortase substrate, and wherein the base layer contacts a solid support.

19. The kit of claim 14, wherein the one or more sortase substrates are attached to the porous membrane.

20. The kit of claim 14, wherein the one or more sortase substrates further comprise one or more peptides comprising the amino acid sequence Leu-Pro-X-Thr-Gly (SEQ ID NO. 1), wherein X may be any proteinogenic amino acid.

21. The kit of claim 14, wherein the one or more sortase substrates further comprise one or more peptides comprising the amino acid sequence Leu-Pro-Asn-Thr-Ala (SEQ ID NO: 3).

22. The kit of claim 20, wherein the proteinogenic amino acid is selected from the group consisting of alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, and tyrosine.

23. The method of claim 1, wherein the one or more sortase substrates further comprise one or more peptides comprising the amino acid sequence Asn-X-Thr-Asn (SEQ ID NO: 2), wherein X may be any proteinogenic amino acid.

24. The method of claim 23, wherein the proteinogenic amino acid is selected from the group consisting of alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, and tyrosine.

25. The kit of claim 14, wherein the one or more sortase substrates further comprise one or more peptides comprising the amino acid sequence Asn-X-Thr-Asn (SEQ ID NO: 2), wherein X may be any proteinogenic amino acid.

26. The kit of claim 25, wherein the proteinogenic amino acid is selected from the group consisting of alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, and tyrosine.

* * * * *

UNITED STATES PATENT AND TRADEMARK OFFICE
CERTIFICATE OF CORRECTION

PATENT NO. : 8,911,961 B2
APPLICATION NO. : 13/823305
DATED : December 16, 2014
INVENTOR(S) : Sjong et al.

Page 1 of 1

It is certified that error appears in the above-identified patent and that said Letters Patent is hereby corrected as shown below:

On the title page; insert -- 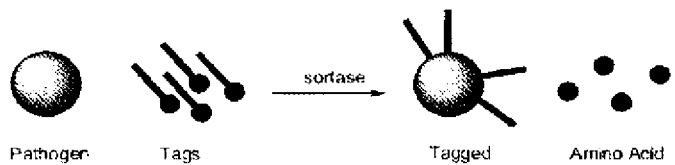 --, therefor.

In the drawings

In Fig. 1, Sheet 1, delete " 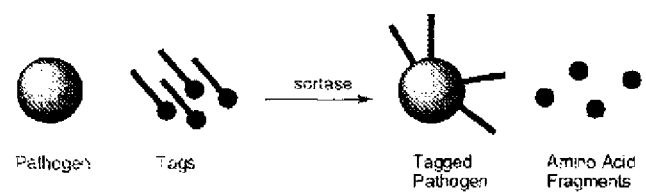 " and insert -- 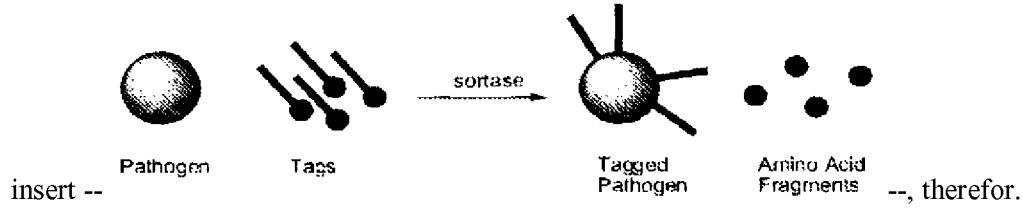 --, therefor.

In the specification

In Column 1, Line 17, delete "7,900" and insert -- 47,900 --, therefor.

In Column 5, Line 31, delete "diphtherias," and insert -- diphtheriae, --, therefor.

Signed and Sealed this
Twenty-ninth Day of December, 2015

Michelle K. Lee
*Director of the United States Patent and Trademark Office*

SEQUENCE LISTING

```
<160> NUMBER OF SEQ ID NOS: 134

<210> SEQ ID NO 1
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      consensus peptide motif sequence
<220> FEATURE:
<221> NAME/KEY: MOD_RES
<222> LOCATION: (3)..(3)
<223> OTHER INFORMATION: Any proteinogenic amino acid

<400> SEQUENCE: 1

Lys Pro Xaa Thr Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide motif sequence
<220> FEATURE:
<221> NAME/KEY: MOD_RES
<222> LOCATION: (2)..(2)
<223> OTHER INFORMATION: Any proteinogenic amino acid

<400> SEQUENCE: 2

Asn Xaa Thr Asn
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide motif sequence

<400> SEQUENCE: 3

Leu Pro Asn Thr Ala
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Pro Lys Asn
1

<210> SEQ ID NO 5
<211> LENGTH: 5
<212> TYPE: PRT
<213> ORGANISM: Lactobacillus johnsonii

<400> SEQUENCE: 5

Leu Pro Gln Thr Gly
1               5

<210> SEQ ID NO 6
<211> LENGTH: 6
<212> TYPE: PRT
<213> ORGANISM: Lactobacillus plantarum
<220> FEATURE:
<221> NAME/KEY: MOD_RES
<222> LOCATION: (5)..(5)
<223> OTHER INFORMATION: Any amino acid
```

```
<400> SEQUENCE: 6

Leu Pro Gln Thr Xaa Glu
1               5

<210> SEQ ID NO 7
<211> LENGTH: 6
<212> TYPE: PRT
<213> ORGANISM: Listeria monocytogenes
<220> FEATURE:
<221> NAME/KEY: MOD_RES
<222> LOCATION: (3)..(3)
<223> OTHER INFORMATION: Any amino acid

<400> SEQUENCE: 7

Leu Pro Xaa Thr Gly Asp
1               5

<210> SEQ ID NO 8
<211> LENGTH: 5
<212> TYPE: PRT
<213> ORGANISM: Streptomyces coelicolor
<220> FEATURE:
<221> NAME/KEY: MOD_RES
<222> LOCATION: (3)..(3)
<223> OTHER INFORMATION: Any amino acid

<400> SEQUENCE: 8

Leu Ala Xaa Thr Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Pro Lys Thr Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Pro Asn Thr Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Pro Glu Thr Gly
1               5

<210> SEQ ID NO 12
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Pro Gln Thr Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Pro Ala Thr Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Pro Asn Thr Ala
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Ala Glu Thr Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Pro Gln Thr Asn
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: Lys, Ala, Asn, Gln, Glu, Thr, Pro, Ser, His,
      Asp, Ile, Arg, Val, Met, Phe, Leu, Tyr or Gly
<220> FEATURE:
<221> NAME/KEY: MOD_RES
<222> LOCATION: (5)..(5)
<223> OTHER INFORMATION: Gly, Ala, Ser, Asp, Asn, Val, Gln, Glu, Lys or
      Pro

<400> SEQUENCE: 17

Leu Pro Xaa Thr Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 18

Leu Pro Xaa Thr Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly
<220> FEATURE:
<221> NAME/KEY: MOD_RES
<222> LOCATION: (4)..(4)
<223> OTHER INFORMATION: Thr, Ala, Lys, Gly, Ser, Tyr, Glu, Met, Val or
      Leu

<400> SEQUENCE: 19

Leu Pro Xaa Xaa Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 20

Leu Pro Xaa Ala Gly
1               5

<210> SEQ ID NO 21
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 21

Leu Pro Xaa Thr Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 22

Leu Pro Xaa Thr Asn
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 23

Leu Ala Xaa Thr Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 24

Leu Ser Xaa Thr Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
       peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 25

Ile Pro Xaa Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 26

Phe Pro Xaa Thr Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 27

Leu Pro Xaa Thr Ala
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Lys Lys Glu Lys
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Pro Lys Thr Gly
1               5
```

```
<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Pro Gln Thr Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Pro Ser Thr Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Pro Asp Thr Ala
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Pro Ala Leu Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Pro Asp Thr Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Ile Pro Glu Thr Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Pro Lys Thr Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Pro Met Thr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Pro Asn Thr Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Pro Gln Thr Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Pro Arg Thr Gly
1               5

<210> SEQ ID NO 41
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 41

Ile Val Lys Thr Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ala Ala Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Ala Asp Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Ala Glu Thr Gly
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Ala His Thr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Ala Phe Thr Gly
1               5
```

```
<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Ala Lys Thr Gly
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Ala Leu Thr Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Ala Asn Thr Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Ala Arg Thr Gly
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Ala Ser Thr Gly
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 52

Leu Ala Tyr Thr Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Ala Glu Thr Pro
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Glu Lys Thr Asn
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Gly Ala Thr Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Gly Asn Thr Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Leu Lys Thr Gly
1               5

<210> SEQ ID NO 58
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 58

Leu Pro Ala Ala Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Pro Glu Ala Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Pro His Ala Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Pro Lys Ala Gly
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Pro Leu Ala Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Pro Asn Ala Gly
1               5
```

```
<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Pro Gln Ala Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Pro Ser Ala Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Pro Thr Ala Gly
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Pro Lys Ala Asn
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Pro Glu Lys Gly
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 69

Leu Pro Ala Leu Gly
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Pro Gln Met Asn
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Pro Asp Thr Ala
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Pro Glu Thr Ala
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Pro Lys Thr Ala
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Pro Asn Thr Ala
1               5

<210> SEQ ID NO 75
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Pro Phe Ser Gly
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Pro Ser Ser Gly
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Pro Gln Thr Asp
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Pro Ala Thr Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Pro Asp Thr Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Pro Glu Thr Gly
```

```
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Pro Phe Thr Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Pro Gly Thr Gly
1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Pro His Thr Gly
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Pro Lys Thr Gly
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Pro Leu Thr Gly
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 86

Leu Pro Met Thr Gly
1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Pro Asn Thr Gly
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Pro Gln Thr Gly
1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Pro Arg Thr Gly
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Pro Ser Thr Gly
1               5

<210> SEQ ID NO 91
<211> LENGTH: 5
<212> TYPE: PRT
<213> ORGANISM: Listeria monocytogenes

<400> SEQUENCE: 91

Leu Pro Thr Thr Gly
1               5

<210> SEQ ID NO 92
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 92

Leu Pro Val Thr Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Leu Pro Tyr Thr Gly
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Pro Lys Thr Asn
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Pro Met Thr Asn
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Pro Gln Thr Asn
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Pro Thr Thr Asn
1               5
```

```
<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Pro Asp Thr Ser
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Pro Lys Thr Ser
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Pro Asn Thr Ser
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Pro Gln Thr Ser
1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Leu Pro Ser Thr Ser
1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 103

Leu Pro Glu Thr Val
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Pro Ile Val Gly
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Pro Ile Tyr Ser
1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu Ser Asn Thr Gly
1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Ser Ser Thr Gly
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Ser Phe Thr Gly
1               5

<210> SEQ ID NO 109
<211> LENGTH: 5
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 109

Asn Ala Lys Thr Asn
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Asn Ala Lys Thr Ser
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Asn Lys Lys Ser Ala
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Asn Pro Lys Thr Gly
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Asn Pro Gln Thr Gly
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Asn Pro Gln Thr Asn
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asn Pro Thr Lys Gln
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asn Pro Lys Ser Ser
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asn Ser Lys Thr Ala
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Pro Glu Thr Gly Glu
1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Pro Lys Thr Gly Glu
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 120

Val Pro Thr Gly Val
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Val Ala Asn Thr Gly
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Val Pro Asp Thr Gly
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Val Pro Pro Thr Gly
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Tyr Pro Lys Thr Gly
1               5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Pro Arg Thr Gly
1               5

<210> SEQ ID NO 126
<211> LENGTH: 6
```

```
<212> TYPE: PRT
<213> ORGANISM: Listeria monocytogenes

<400> SEQUENCE: 126

Leu Pro Lys Thr Gly Asp
1               5

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Leu Pro Thr Thr Gly Lys Lys Lys Lys Lys
1               5                   10

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Lys Lys Lys Lys Lys
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Pro Ile Thr Gly
1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Leu Pro Asn Thr Asn
1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asn Asp Thr Ala Val
1               5
```

```
<210> SEQ ID NO 132
<211> LENGTH: 771
<212> TYPE: PRT
<213> ORGANISM: Listeria monocytogenes

<400> SEQUENCE: 132
```

| | | | | | | | | | | | | | | |
|---|---|---|---|---|---|---|---|---|---|---|---|---|---|---|
| Met | Arg | Lys | Lys | Arg | Tyr | Val | Trp | Leu | Lys | Ser | Ile | Leu | Val | Ala | Ile |
| 1 | | | | 5 | | | | | 10 | | | | | 15 |
| Leu | Val | Phe | Gly | Ser | Gly | Val | Trp | Ile | Asn | Thr | Ser | Asn | Gly | Thr | Asn |
| | | | 20 | | | | | 25 | | | | | 30 | |
| Ala | Gln | Ala | Ala | Thr | Ile | Thr | Gln | Asp | Thr | Pro | Ile | Asn | Gln | Ile | Phe |
| | | | 35 | | | | 40 | | | | | 45 | | |
| Thr | Asp | Thr | Ala | Leu | Ala | Glu | Lys | Met | Lys | Thr | Val | Leu | Gly | Lys | Thr |
| 50 | | | | | 55 | | | | | 60 | | | | |
| Asn | Val | Thr | Asp | Thr | Val | Ser | Gln | Thr | Asp | Leu | Asp | Gln | Val | Thr | Thr |
| 65 | | | | 70 | | | | | 75 | | | | | 80 |
| Leu | Gln | Ala | Asp | Arg | Leu | Gly | Ile | Lys | Ser | Ile | Asp | Gly | Val | Glu | Tyr |
| | | | | 85 | | | | | 90 | | | | | 95 |
| Leu | Asn | Asn | Leu | Thr | Gln | Ile | Asn | Phe | Ser | Asn | Asn | Gln | Leu | Thr | Asp |
| | | | 100 | | | | 105 | | | | | 110 | | |
| Ile | Thr | Pro | Leu | Lys | Asn | Leu | Thr | Lys | Leu | Val | Asp | Ile | Leu | Met | Asn |
| | | 115 | | | | | 120 | | | | | 125 | | |
| Asn | Asn | Gln | Ile | Ala | Asp | Ile | Thr | Pro | Leu | Ala | Asn | Leu | Thr | Asn | Leu |
| 130 | | | | | 135 | | | | | 140 | | | | |
| Thr | Gly | Leu | Thr | Leu | Phe | Asn | Asn | Gln | Ile | Thr | Asp | Ile | Asp | Pro | Leu |
| 145 | | | | 150 | | | | | 155 | | | | | 160 |
| Lys | Asn | Leu | Thr | Asn | Leu | Asn | Arg | Leu | Glu | Leu | Ser | Ser | Asn | Thr | Ile |
| | | | | 165 | | | | | 170 | | | | | 175 |
| Ser | Asp | Ile | Ser | Ala | Leu | Ser | Gly | Leu | Thr | Ser | Leu | Gln | Gln | Leu | Ser |
| | | | 180 | | | | | 185 | | | | | 190 | |
| Phe | Gly | Asn | Gln | Val | Thr | Asp | Leu | Lys | Pro | Leu | Ala | Asn | Leu | Thr | Thr |
| | | | 195 | | | | | 200 | | | | | 205 | |
| Leu | Glu | Arg | Leu | Asp | Ile | Ser | Ser | Asn | Lys | Val | Ser | Asp | Ile | Ser | Val |
| 210 | | | | | 215 | | | | | 220 | | | | |
| Leu | Ala | Lys | Leu | Thr | Asn | Leu | Glu | Ser | Leu | Ile | Ala | Thr | Asn | Asn | Gln |
| 225 | | | | | 230 | | | | | 235 | | | | | 240 |
| Ile | Ser | Asp | Ile | Thr | Pro | Leu | Gly | Ile | Leu | Thr | Asn | Leu | Asp | Glu | Leu |
| | | | | 245 | | | | | 250 | | | | | 255 |
| Ser | Leu | Asn | Gly | Asn | Gln | Leu | Lys | Asp | Ile | Gly | Thr | Leu | Ala | Ser | Leu |
| | | | 260 | | | | | 265 | | | | | 270 | |
| Thr | Asn | Leu | Thr | Asp | Leu | Asp | Leu | Ala | Asn | Asn | Gln | Ile | Ser | Asn | Leu |
| | | | 275 | | | | | 280 | | | | | 285 | |
| Ala | Pro | Leu | Ser | Gly | Leu | Thr | Lys | Leu | Thr | Glu | Leu | Lys | Leu | Gly | Ala |
| | 290 | | | | | 295 | | | | | 300 | | | | |
| Asn | Gln | Ile | Ser | Asn | Ile | Ser | Pro | Leu | Ala | Gly | Leu | Thr | Ala | Leu | Thr |
| 305 | | | | | 310 | | | | | 315 | | | | | 320 |
| Asn | Leu | Glu | Leu | Asn | Glu | Asn | Gln | Leu | Glu | Asp | Ile | Ser | Pro | Ile | Ser |
| | | | | 325 | | | | | 330 | | | | | 335 |
| Asn | Leu | Lys | Asn | Leu | Thr | Tyr | Leu | Thr | Leu | Tyr | Phe | Asn | Asn | Ile | Ser |
| | | | 340 | | | | | 345 | | | | | 350 | |
| Asp | Ile | Ser | Pro | Val | Ser | Ser | Leu | Thr | Lys | Leu | Gln | Arg | Leu | Phe | Phe |
| | | | 355 | | | | | 360 | | | | | 365 | |
| Tyr | Asn | Asn | Lys | Val | Ser | Asp | Val | Ser | Ser | Leu | Ala | Asn | Leu | Thr | Asn |
| 370 | | | | | 375 | | | | | 380 | | | | | |

```
Ile Asn Trp Leu Ser Ala Gly His Asn Gln Ile Ser Asp Leu Thr Pro
385                 390                 395                 400

Leu Ala Asn Leu Thr Arg Ile Thr Gln Leu Gly Leu Asn Asp Gln Ala
            405                 410                 415

Trp Thr Asn Ala Pro Val Asn Tyr Lys Ala Asn Val Ser Ile Pro Asn
                420                 425                 430

Thr Val Lys Asn Val Thr Gly Ala Leu Ile Ala Pro Ala Thr Ile Ser
        435                 440                 445

Asp Gly Gly Ser Tyr Thr Glu Pro Asp Ile Thr Trp Asn Leu Pro Ser
    450                 455                 460

Tyr Thr Asn Glu Val Ser Tyr Thr Phe Ser Gln Pro Val Thr Ile Gly
465                 470                 475                 480

Lys Gly Thr Thr Thr Phe Ser Gly Thr Val Thr Gln Pro Leu Lys Ala
                485                 490                 495

Ile Phe Asn Val Lys Phe His Val Asp Gly Lys Glu Thr Thr Lys Glu
                500                 505                 510

Val Glu Ala Gly Asn Leu Leu Thr Glu Pro Ala Lys Pro Val Lys Glu
            515                 520                 525

Gly His Thr Phe Val Gly Trp Phe Asp Ala Gln Thr Gly Gly Thr Lys
    530                 535                 540

Trp Asn Phe Ser Thr Asp Lys Met Pro Thr Asn Asp Ile Asn Leu Tyr
545                 550                 555                 560

Ala Gln Phe Ser Ile Asn Ser Tyr Thr Ala Thr Phe Asp Asn Asp Gly
                565                 570                 575

Val Thr Thr Ser Gln Thr Val Asp Tyr Gln Gly Leu Leu Gln Glu Pro
            580                 585                 590

Thr Ala Pro Thr Lys Glu Gly Tyr Thr Phe Lys Gly Trp Tyr Asp Ala
    595                 600                 605

Lys Thr Gly Gly Asp Lys Trp Asp Phe Ala Thr Ser Lys Met Pro Ala
    610                 615                 620

Lys Asn Ile Thr Leu Tyr Ala Gln Tyr Ser Ala Asn Ser Tyr Thr Ala
625                 630                 635                 640

Thr Phe Asp Val Asp Gly Lys Ser Thr Thr Gln Ala Val Asp Tyr Gln
            645                 650                 655

Gly Leu Leu Lys Glu Pro Lys Ala Pro Thr Lys Ala Gly Tyr Thr Phe
            660                 665                 670

Lys Gly Trp Tyr Asp Glu Lys Thr Asp Gly Lys Lys Trp Asp Phe Ala
    675                 680                 685

Thr Asp Lys Met Pro Ala Asn Asp Ile Thr Leu Tyr Ala Gln Phe Thr
    690                 695                 700

Lys Asn Pro Val Ala Pro Pro Thr Thr Gly Gly Asn Thr Pro Pro Thr
705                 710                 715                 720

Thr Asn Asn Gly Gly Asn Thr Thr Pro Pro Ser Ala Asn Ile Pro Gly
            725                 730                 735

Ser Asp Thr Ser Asn Thr Ser Thr Gly Asn Ser Ala Ser Thr Thr Ser
        740                 745                 750

Thr Met Asn Ala Tyr Asp Pro Tyr Asn Ser Lys Glu Ala Ser Leu Pro
            755                 760                 765

Thr Thr Gly
    770

<210> SEQ ID NO 133
<211> LENGTH: 776
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 133

Met Arg Lys Lys Arg Tyr Val Trp Leu Lys Ser Ile Leu Val Ala Ile
1               5                   10                  15

Leu Val Phe Gly Ser Gly Val Trp Ile Asn Thr Ser Asn Gly Thr Asn
            20                  25                  30

Ala Gln Ala Ala Thr Ile Thr Gln Asp Thr Pro Ile Asn Gln Ile Phe
        35                  40                  45

Thr Asp Thr Ala Leu Ala Glu Lys Met Lys Thr Val Leu Gly Lys Thr
    50                  55                  60

Asn Val Thr Asp Thr Val Ser Gln Thr Asp Leu Asp Gln Val Thr Thr
65                  70                  75                  80

Leu Gln Ala Asp Arg Leu Gly Ile Lys Ser Ile Asp Gly Val Glu Tyr
                85                  90                  95

Leu Asn Asn Leu Thr Gln Ile Asn Phe Ser Asn Asn Gln Leu Thr Asp
            100                 105                 110

Ile Thr Pro Leu Lys Asn Leu Thr Lys Leu Val Asp Ile Leu Met Asn
        115                 120                 125

Asn Asn Gln Ile Ala Asp Ile Thr Pro Leu Ala Asn Leu Thr Asn Leu
    130                 135                 140

Thr Gly Leu Thr Leu Phe Asn Asn Gln Ile Thr Asp Ile Asp Pro Leu
145                 150                 155                 160

Lys Asn Leu Thr Asn Leu Asn Arg Leu Glu Leu Ser Ser Asn Thr Ile
                165                 170                 175

Ser Asp Ile Ser Ala Leu Ser Gly Leu Thr Ser Leu Gln Gln Leu Ser
            180                 185                 190

Phe Gly Asn Gln Val Thr Asp Leu Lys Pro Leu Ala Asn Leu Thr Thr
        195                 200                 205

Leu Glu Arg Leu Asp Ile Ser Ser Asn Lys Val Ser Asp Ile Ser Val
    210                 215                 220

Leu Ala Lys Leu Thr Asn Leu Glu Ser Leu Ile Ala Thr Asn Asn Gln
225                 230                 235                 240

Ile Ser Asp Ile Thr Pro Leu Gly Ile Leu Thr Asn Leu Asp Glu Leu
                245                 250                 255

Ser Leu Asn Gly Asn Gln Leu Lys Asp Ile Gly Thr Leu Ala Ser Leu
            260                 265                 270

Thr Asn Leu Thr Asp Leu Asp Leu Ala Asn Asn Gln Ile Ser Asn Leu
        275                 280                 285

Ala Pro Leu Ser Gly Leu Thr Lys Leu Thr Gly Leu Lys Leu Gly Ala
    290                 295                 300

Asn Gln Ile Ser Asn Ile Ser Pro Leu Ala Gly Leu Thr Ala Leu Thr
305                 310                 315                 320

Asn Leu Glu Leu Asn Glu Asn Gln Leu Glu Asp Ile Ser Pro Ile Ser
                325                 330                 335

Asn Leu Lys Asn Leu Thr Tyr Leu Thr Leu Tyr Phe Asn Asn Ile Ser
            340                 345                 350

Asp Ile Ser Pro Val Ser Ser Leu Thr Lys Leu Gln Arg Leu Phe Phe
        355                 360                 365

Tyr Asn Asn Lys Val Ser Asp Val Ser Ser Leu Ala Asn Leu Thr Asn
    370                 375                 380

```
Ile Asn Trp Leu Ser Ala Gly His Asn Gln Ile Ser Asp Leu Thr Pro
385                 390                 395                 400

Leu Ala Asn Leu Thr Arg Ile Thr Gln Leu Gly Leu Asn Asp Gln Ala
            405                 410                 415

Trp Thr Asn Ala Pro Val Asn Tyr Lys Ala Asn Val Ser Ile Pro Asn
        420                 425                 430

Thr Val Lys Asn Val Thr Gly Ala Leu Ile Ala Pro Ala Thr Ile Ser
    435                 440                 445

Asp Gly Gly Ser Tyr Thr Glu Pro Asp Ile Thr Trp Asn Leu Pro Ser
450                 455                 460

Tyr Thr Asn Glu Val Ser Tyr Thr Phe Ser Gln Pro Val Thr Ile Gly
465                 470                 475                 480

Lys Gly Thr Thr Thr Phe Ser Gly Thr Val Thr Gln Pro Leu Lys Ala
                485                 490                 495

Ile Phe Asn Val Lys Phe His Val Asp Gly Lys Glu Thr Thr Lys Glu
            500                 505                 510

Val Glu Ala Gly Asn Leu Leu Thr Glu Pro Ala Lys Pro Val Lys Glu
        515                 520                 525

Gly His Thr Phe Val Gly Trp Phe Asp Ala Gln Thr Gly Gly Thr Lys
    530                 535                 540

Trp Asn Phe Ser Thr Asp Lys Met Pro Thr Asn Asp Ile Asn Leu Tyr
545                 550                 555                 560

Ala Gln Phe Ser Ile Asn Ser Tyr Thr Ala Thr Phe Asp Asn Asp Gly
                565                 570                 575

Val Thr Thr Ser Gln Thr Val Asp Tyr Gln Gly Leu Leu Gln Glu Pro
            580                 585                 590

Thr Ala Pro Thr Lys Glu Gly Tyr Thr Phe Lys Gly Trp Tyr Asp Ala
        595                 600                 605

Lys Thr Gly Gly Asp Lys Trp Asp Phe Ala Thr Ser Lys Met Pro Ala
    610                 615                 620

Lys Asn Ile Thr Leu Tyr Ala Gln Tyr Ser Ala Asn Ser Tyr Thr Ala
625                 630                 635                 640

Thr Phe Asp Val Asp Gly Lys Ser Thr Thr Gln Ala Val Asp Tyr Gln
                645                 650                 655

Gly Leu Leu Lys Glu Pro Lys Ala Pro Thr Lys Ala Gly Tyr Thr Phe
            660                 665                 670

Lys Gly Trp Tyr Asp Glu Lys Thr Asp Gly Lys Trp Asp Phe Ala
        675                 680                 685

Thr Asp Lys Met Pro Ala Asn Asp Ile Thr Leu Tyr Ala Gln Phe Thr
    690                 695                 700

Lys Asn Pro Val Ala Pro Thr Thr Gly Gly Asn Thr Pro Pro Thr
705                 710                 715                 720

Thr Asn Asn Gly Gly Asn Thr Thr Pro Pro Ser Ala Asn Ile Pro Gly
                725                 730                 735

Ser Asp Thr Ser Asn Thr Ser Thr Gly Asn Ser Ala Ser Thr Thr Ser
            740                 745                 750

Thr Met Asn Ala Tyr Asp Pro Tyr Asn Ser Lys Glu Ala Ser Leu Pro
        755                 760                 765

Thr Thr Gly Lys Lys Lys Lys Lys
    770                 775

<210> SEQ ID NO 134
```

```
<211> LENGTH: 800
<212> TYPE: PRT
<213> ORGANISM: Listeria monocytogenes

<400> SEQUENCE: 134
```

| | |

-continued

```
Ile Asn Trp Leu Ser Ala Gly His Asn Gln Ile Ser Asp Leu Thr Pro
385                 390                 395                 400

Leu Ala Asn Leu Thr Arg Ile Thr Gln Leu Gly Leu Asn Asp Gln Ala
            405                 410                 415

Trp Thr Asn Ala Pro Val Asn Tyr Lys Ala Asn Val Ser Ile Pro Asn
        420                 425                 430

Thr Val Lys Asn Val Thr Gly Ala Leu Ile Ala Pro Ala Thr Ile Ser
            435                 440                 445

Asp Gly Gly Ser Tyr Thr Glu Pro Asp Ile Thr Trp Asn Leu Pro Ser
        450                 455                 460

Tyr Thr Asn Glu Val Ser Tyr Thr Phe Ser Gln Pro Val Thr Ile Gly
465                 470                 475                 480

Lys Gly Thr Thr Thr Phe Ser Gly Thr Val Thr Gln Pro Leu Lys Ala
            485                 490                 495

Ile Phe Asn Val Lys Phe His Val Asp Gly Lys Glu Thr Thr Lys Glu
        500                 505                 510

Val Glu Ala Gly Asn Leu Leu Thr Glu Pro Ala Lys Pro Val Lys Glu
            515                 520                 525

Gly His Thr Phe Val Gly Trp Phe Asp Ala Gln Thr Gly Gly Thr Lys
        530                 535                 540

Trp Asn Phe Ser Thr Asp Lys Met Pro Thr Asn Asp Ile Asn Leu Tyr
545                 550                 555                 560

Ala Gln Phe Ser Ile Asn Ser Tyr Thr Ala Thr Phe Asp Asn Asp Gly
            565                 570                 575

Val Thr Thr Ser Gln Thr Val Asp Tyr Gln Gly Leu Leu Gln Glu Pro
        580                 585                 590

Thr Ala Pro Thr Lys Glu Gly Tyr Thr Phe Lys Gly Trp Tyr Asp Ala
            595                 600                 605

Lys Thr Gly Gly Asp Lys Trp Asp Phe Ala Thr Ser Lys Met Pro Ala
        610                 615                 620

Lys Asn Ile Thr Leu Tyr Ala Gln Tyr Ser Ala Asn Ser Tyr Thr Ala
625                 630                 635                 640

Thr Phe Asp Val Asp Gly Lys Ser Thr Thr Gln Ala Val Asp Tyr Gln
            645                 650                 655

Gly Leu Leu Lys Glu Pro Lys Ala Pro Thr Lys Ala Gly Tyr Thr Phe
        660                 665                 670

Lys Gly Trp Tyr Asp Glu Lys Thr Asp Gly Lys Lys Trp Asp Phe Ala
            675                 680                 685

Thr Asp Lys Met Pro Ala Asn Asp Ile Thr Leu Tyr Ala Gln Phe Thr
        690                 695                 700

Lys Asn Pro Val Ala Pro Pro Thr Thr Gly Gly Asn Thr Pro Pro Thr
705                 710                 715                 720

Thr Asn Asn Gly Gly Asn Thr Thr Pro Pro Ser Ala Asn Ile Pro Gly
            725                 730                 735

Ser Asp Thr Ser Asn Thr Ser Thr Gly Asn Ser Ala Ser Thr Thr Ser
        740                 745                 750

Thr Met Asn Ala Tyr Asp Pro Tyr Asn Ser Lys Glu Ala Ser Leu Pro
            755                 760                 765

Thr Thr Gly Asp Ser Asp Asn Ala Leu Tyr Leu Leu Leu Gly Leu Leu
        770                 775                 780

Ala Val Gly Thr Ala Met Ala Leu Thr Lys Lys Ala Arg Ala Ser Lys
785                 790                 795                 800
```